US011717356B2

(12) United States Patent
Amiri et al.

(10) Patent No.: US 11,717,356 B2
(45) Date of Patent: *Aug. 8, 2023

(54) SYSTEM AND METHOD OF AUTOMATIC DETECTION OF OBSTRUCTIONS FOR A ROBOTIC CATHETER SYSTEM

(71) Applicant: St. Jude Medical, Atrial Fibrillation Division Inc, St. Paul, MN (US)

(72) Inventors: Atila Amiri, Fremont, CA (US); Kulbir S. Sandhu, Singapore (SG); Betty Mark, Sunnyvale, CA (US); Mark B. Kirschenman, Waverly, MN (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 920 days.

This patent is subject to a terminal disclaimer.

(21) Appl. No.: 16/540,944

(22) Filed: Aug. 14, 2019

(65) Prior Publication Data

US 2020/0038122 A1    Feb. 6, 2020

Related U.S. Application Data

(63) Continuation of application No. 15/089,791, filed on Apr. 4, 2016, now Pat. No. 10,426,557, which is a
(Continued)

(51) Int. Cl.
    *A61B 34/30*      (2016.01)
    *A61B 34/37*      (2016.01)
(Continued)

(52) U.S. Cl.
    CPC ............. *A61B 34/30* (2016.02); *A61B 34/37* (2016.02); *A61B 34/71* (2016.02); *A61B 34/76* (2016.02);
(Continued)

(58) Field of Classification Search
    CPC ......... A61B 34/30; A61B 34/37; A61B 34/71; A61B 34/76; A61B 34/77; A61B 90/06;
(Continued)

(56) References Cited

U.S. PATENT DOCUMENTS 3,091,130 A    5/1963   Payerle et al.
3,605,725 A    9/1971   Bentov
(Continued)

FOREIGN PATENT DOCUMENTS

EP        0151479      8/1985
EP        0904796      3/1999
(Continued)

OTHER PUBLICATIONS

Title: Supplemental European Search Report Citation: EP Application No. 11763450.1 dated Oct. 29, 2014 9 pages.
(Continued)

*Primary Examiner* — Lauren P Farrar
*Assistant Examiner* — Hamza A Darb
(74) *Attorney, Agent, or Firm* — Billion & Armitage

(57) ABSTRACT

An obstruction detection system for a robotic catheter system including a robotic catheter manipulator assembly including one or more catheter manipulation bases and one or more sheath manipulation bases. Each manipulation base may be generally linearly movable on one or more tracks relative to the robotic catheter manipulator assembly. The obstruction detection system may include one or more obstruction detection sensors disposed on the track or on the manipulation bases to detect an obstruction along a path of motion of one or more manipulation bases. A software system may be provided for monitoring movement of the catheter and sheath manipulation bases, and/or a status of the obstruction detection sensors.

18 Claims, 11 Drawing Sheets

Related U.S. Application Data continuation of application No. 13/120,715, filed as application No. PCT/US2009/058121 on Sep. 23, 2009, now Pat. No. 9,301,810, which is a continuation of application No. 12/347,835, filed on Dec. 31, 2008, now Pat. No. 8,684,962, and a continuation of application No. 12/347,826, filed on Dec. 31, 2008, now Pat. No. 8,317,744, and a continuation of application No. 12/347,842, filed on Dec. 31, 2008, now Pat. No. 8,317,745, and a continuation of application No. 12/347,811, filed on Dec. 31, 2008, now Pat. No. 8,343,096.

(60) Provisional application No. 61/099,904, filed on Sep. 24, 2008, provisional application No. 61/040,143, filed on Mar. 27, 2008.

(51) Int. Cl.
```
A61B 34/00      (2016.01)
A61B 34/20      (2016.01)
A61B 90/00      (2016.01)
A61B 18/00      (2006.01)
A61M 25/01      (2006.01)
A61B 18/14      (2006.01)
A61B 17/00      (2006.01)
```

(52) U.S. Cl.
CPC .............. *A61B 34/77* (2016.02); *A61B 90/06* (2016.02); *A61M 25/0113* (2013.01); *A61M 25/0147* (2013.01); *A61B 18/1492* (2013.01); *A61B 34/20* (2016.02); *A61B 2017/00026* (2013.01); *A61B 2017/00477* (2013.01); *A61B 2018/00351* (2013.01); *A61B 2018/00577* (2013.01); *A61B 2018/00642* (2013.01); *A61B 2034/2055* (2016.02); *A61B 2034/301* (2016.02); *A61B 2034/305* (2016.02); *A61B 2034/741* (2016.02); *A61B 2034/742* (2016.02); *A61B 2090/064* (2016.02)

(58) Field of Classification Search
CPC ................ A61B 18/1492; A61B 34/20; A61B 2017/00026; A61B 2017/00477; A61B 2018/00351; A61B 2018/00577; A61B 2018/00642; A61B 2034/2055; A61B 2034/301; A61B 2034/305; A61B 2034/741; A61B 2034/742; A61B 2090/064; A61M 25/0113; A61M 25/0147
See application file for complete search history.

(56) References Cited

U.S. PATENT DOCUMENTS

| | | |
|---|---|---|
| 3,893,449 A | 7/1975 | Lee et al. |
| 4,180,508 A | 7/1979 | Frosch et al. |
| 4,348,556 A | 9/1982 | Gettig et al. |
| 4,393,728 A | 7/1983 | Larson et al. |
| 4,494,417 A | 1/1985 | Larson |
| 4,543,090 A | 9/1985 | McCoy |
| 4,758,222 A | 7/1988 | McCoy |
| 4,784,042 A | 11/1988 | Paynter |
| 4,802,487 A | 2/1989 | Martin |
| 4,884,557 A | 12/1989 | Takehana |
| 4,962,448 A | 10/1990 | DeMaio |
| 4,974,151 A | 11/1990 | Advani et al. |
| 5,078,140 A | 1/1992 | Kwoh |
| 5,107,080 A | 4/1992 | Rosen |
| 5,170,817 A | 12/1992 | Sunderland |
| 5,238,005 A | 8/1993 | Imran |
| 5,298,930 A * | 3/1994 | Asakura ............... G03B 17/425 396/387 |
| 5,303,148 A | 4/1994 | Mattson et al. |
| 5,318,525 A | 6/1994 | West |
| 5,339,799 A | 8/1994 | Kami et al. |
| 5,396,266 A | 3/1995 | Brimhall et al. |
| 5,410,838 A | 4/1995 | Colgate et al. |
| 5,441,483 A | 8/1995 | Avitall |
| 5,449,345 A | 9/1995 | Taylor |
| 5,520,844 A | 5/1996 | Imran |
| 5,533,967 A | 7/1996 | Imran |
| 5,545,200 A | 8/1996 | West |
| 5,579,442 A | 11/1996 | Kimoto |
| 5,607,158 A | 3/1997 | Chan |
| 5,607,462 A | 3/1997 | Imran |
| 5,623,582 A | 4/1997 | Rosenberg |
| 5,630,783 A | 5/1997 | Steinberg |
| 5,661,253 A | 8/1997 | Aoki |
| 5,706,827 A | 1/1998 | Ehr |
| 5,784,542 A | 7/1998 | Ohm |
| 5,791,908 A | 8/1998 | Gillio |
| 5,800,178 A | 9/1998 | Gillio |
| 5,807,377 A | 9/1998 | Madhani |
| 5,808,665 A | 9/1998 | Green |
| 5,828,813 A | 10/1998 | Ohm |
| 5,854,622 A | 12/1998 | Brannon |
| 5,861,024 A | 1/1999 | Rashidi |
| 5,876,325 A | 3/1999 | Mizuno et al. |
| 5,897,488 A | 4/1999 | Ueda |
| 5,913,820 A | 6/1999 | Bladen et al. |
| 6,040,758 A | 3/2000 | Sedor |
| 6,063,095 A | 5/2000 | Wang |
| 6,113,395 A | 9/2000 | Hon |
| 6,201,196 B1 | 3/2001 | Wergen |
| 6,233,476 B1 | 5/2001 | Strommer et al. |
| 6,233,504 B1 | 5/2001 | Das et al. |
| 6,290,683 B1 | 9/2001 | Erez |
| 6,348,911 B1 | 2/2002 | Rosenberg |
| 6,368,207 B1 | 3/2002 | Lathbury et al. |
| 6,385,509 B2 | 5/2002 | Das et al. |
| 6,398,232 B1 | 5/2002 | Haanpaa |
| 6,432,112 B2 | 8/2002 | Brock |
| 6,498,944 B1 | 12/2002 | Ben-Haim et al. |
| 6,500,167 B1 | 12/2002 | Webster |
| 6,522,141 B2 | 2/2003 | Debblns et al. |
| 6,540,685 B1 | 4/2003 | Rhoads et al. |
| 6,671,533 B2 | 12/2003 | Chen et al. |
| 6,709,667 B1 | 3/2004 | Lowe |
| 6,785,358 B2 | 8/2004 | Johnson |
| 6,850,252 B1 | 2/2005 | Hoffberg |
| 6,869,390 B2 | 3/2005 | Elliott |
| 6,869,396 B2 | 3/2005 | Belson |
| 6,968,223 B2 | 11/2005 | Hanover |
| 7,016,469 B2 | 3/2006 | Johnson et al. |
| 7,193,521 B2 | 3/2007 | Moberg |
| 7,197,354 B2 | 3/2007 | Sobe |
| 7,199,790 B2 | 4/2007 | Rosenberg |
| 7,247,139 B2 | 7/2007 | Yudkovitch et al. |
| 7,263,397 B2 | 8/2007 | Hauck |
| 7,276,044 B2 | 10/2007 | Ferry |
| 7,386,339 B2 | 6/2008 | Strommer et al. |
| 7,465,288 B2 | 12/2008 | Dudney et al. |
| 7,672,849 B2 | 3/2010 | Yudkovitch |
| 7,698,966 B2 | 4/2010 | Gosselin |
| 7,742,803 B2 | 6/2010 | Viswanathan et al. |
| 7,850,642 B2 | 12/2010 | Moll |
| 7,880,717 B2 | 2/2011 | Berkley et al. |
| 7,945,546 B2 | 5/2011 | Bliss et al. |
| 7,963,288 B2 | 6/2011 | Rosenberg et al. |
| 8,164,573 B2 | 4/2012 | DaCosta et al. |
| 8,317,744 B2 | 11/2012 | Kirschenman |
| 8,317,745 B2 | 11/2012 | Kirschenman |
| 8,332,072 B1 | 12/2012 | Schaible et al. |
| 8,390,438 B2 | 3/2013 | Olson |
| 8,416,203 B2 | 4/2013 | Tsui |
| 8,560,118 B2 | 10/2013 | Greer et al. |
| 8,926,511 B2 | 1/2015 | Bar-Tar |
| 9,301,810 B2 * | 4/2016 | Amiri .................... A61B 90/06 |
| 2001/0018591 A1 | 8/2001 | Brock |
| 2001/0025183 A1 | 9/2001 | Shahidi |
| 2002/0065485 A1 | 5/2002 | DuBois et al. |

(56) References Cited

U.S. PATENT DOCUMENTS

| | | |
|---|---|---|
| 2002/0068868 A1 | 6/2002 | Thompson et al. |
| 2002/0072704 A1 | 6/2002 | Mansouri-Ruiz |
| 2002/0087048 A1 | 7/2002 | Brock |
| 2002/0184055 A1 | 12/2002 | Naghavi et al. |
| 2003/0018232 A1 | 1/2003 | Elliott |
| 2003/0050733 A1 | 3/2003 | Wang et al. |
| 2003/0114962 A1 | 6/2003 | Niemeyer |
| 2003/0121382 A1 | 7/2003 | Morson |
| 2004/0050247 A1 | 3/2004 | Topping |
| 2004/0068173 A1 | 4/2004 | Viswanathan |
| 2004/0133189 A1 | 7/2004 | Sakurai |
| 2004/0138530 A1 | 7/2004 | Kawai |
| 2004/0146388 A1 | 7/2004 | Khajepour et al. |
| 2004/0183239 A1 | 9/2004 | Falwell et al. |
| 2004/0223636 A1 | 11/2004 | Edic |
| 2004/0243147 A1 | 12/2004 | Lipow |
| 2005/0038333 A1 | 2/2005 | Sra |
| 2005/0075538 A1 | 4/2005 | Banik |
| 2005/0172405 A1 | 8/2005 | Menkedick et al. |
| 2005/0203382 A1 | 9/2005 | Govari |
| 2005/0222554 A1 | 10/2005 | Wallace |
| 2005/0234293 A1 | 10/2005 | Yamamoto et al. |
| 2005/0234320 A1 | 10/2005 | Balasubramanian |
| 2006/0052664 A1 | 3/2006 | Julian |
| 2006/0089637 A1 | 4/2006 | Werneth et al. |
| 2006/0137476 A1 | 6/2006 | Bull |
| 2006/0155321 A1 | 7/2006 | Bressler et al. |
| 2006/0276775 A1 | 12/2006 | Rosenberg et al. |
| 2007/0016008 A1 | 1/2007 | Schoenefeld |
| 2007/0022384 A1 | 1/2007 | Abbott et al. |
| 2007/0043338 A1 | 2/2007 | Moll et al. |
| 2007/0060833 A1 | 3/2007 | Hauck |
| 2007/0073137 A1 | 3/2007 | Schoenefeld |
| 2007/0100254 A1 | 5/2007 | Murakami et al. |
| 2007/0120512 A1 | 5/2007 | Albu-Schaffer |
| 2007/0135803 A1 | 6/2007 | Belson |
| 2007/0142726 A1 | 6/2007 | Carney |
| 2007/0172803 A1 | 7/2007 | Hannaford et al. |
| 2007/0185404 A1 | 8/2007 | Hauck et al. |
| 2007/0185485 A1 | 8/2007 | Hauck |
| 2007/0185486 A1 | 8/2007 | Hauck |
| 2007/0197896 A1 | 8/2007 | Moll et al. |
| 2007/0197939 A1 | 8/2007 | Wallace |
| 2007/0198008 A1 | 8/2007 | Hauck et al. |
| 2007/0233044 A1 | 10/2007 | Wailace |
| 2007/0233045 A1 | 10/2007 | Weitzner |
| 2007/0257821 A1 | 11/2007 | Son et al. |
| 2007/0268269 A1 | 11/2007 | Chang et al. |
| 2007/0270685 A1 | 11/2007 | Kang |
| 2007/0276214 A1 | 11/2007 | Dachille |
| 2007/0298877 A1 | 12/2007 | Rosenberg et al. |
| 2008/0009791 A1 | 1/2008 | Cohen et al. |
| 2008/0013809 A1 | 1/2008 | Zhu |
| 2008/0112842 A1 | 5/2008 | Edwards |
| 2008/0201847 A1* | 8/2008 | Menkedick .......... A61G 7/0507 5/600 |
| 2008/0297490 A1 | 12/2008 | Adkins |
| 2008/0312536 A1 | 12/2008 | Dala-Krishna |
| 2009/0012533 A1 | 1/2009 | Barbagli |
| 2009/0033623 A1 | 2/2009 | Lin |
| 2009/0061928 A1 | 3/2009 | Lee et al. |
| 2009/0123111 A1 | 5/2009 | Udd |
| 2009/0137952 A1 | 5/2009 | Ramamurthy et al. |
| 2009/0177454 A1 | 7/2009 | Bronstein |
| 2009/0192519 A1 | 7/2009 | Omori et al. |
| 2009/0195514 A1 | 8/2009 | Glynn et al. |
| 2009/0247993 A1 | 10/2009 | Kirschenman et al. |
| 2009/0264156 A1 | 10/2009 | Burghardt et al. |
| 2009/0322697 A1 | 12/2009 | Cao |
| 2009/0327886 A1 | 12/2009 | Whytock |
| 2010/0066676 A1 | 3/2010 | Kramer et al. |
| 2010/0073150 A1 | 3/2010 | Olson et al. |
| 2010/0079386 A1 | 4/2010 | Scott et al. |
| 2010/0082039 A1 | 4/2010 | Mohr et al. |
| 2010/0103127 A1 | 4/2010 | Park et al. |
| 2010/0256558 A1 | 10/2010 | Olson et al. |
| 2010/0268067 A1 | 10/2010 | Razzaque et al. |
| 2010/0314031 A1 | 12/2010 | Heideman et al. |
| 2011/0040547 A1 | 2/2011 | Gerber et al. |
| 2011/0128555 A1 | 6/2011 | Rotschild |
| 2011/0137156 A1 | 6/2011 | Razzaque et al. |
| 2011/0152882 A1 | 6/2011 | Wenderow et al. |
| 2011/0289441 A1 | 11/2011 | Venon et al. |
| 2011/0306986 A1 | 12/2011 | Lee et al. |
| 2012/0071891 A1 | 3/2012 | Itkowitz et al. |
| 2012/0133601 A1 | 5/2012 | Marshall et al. |
| 2012/0277663 A1 | 11/2012 | Millman et al. |
| 2013/0006268 A1 | 1/2013 | Swarup et al. |
| 2013/0154913 A1 | 6/2013 | Genc et al. |
| 2013/0165854 A1 | 6/2013 | Sandhu et al. |
| 2013/0176220 A1 | 7/2013 | Merschon et al. |
| 2013/0179162 A1 | 7/2013 | Merschon et al. |

FOREIGN PATENT DOCUMENTS

| | | | |
|---|---|---|---|
| GB | 2211280 | 6/1989 | |
| GB | 2397177 | 7/2007 | |
| JP | S60221280 | 11/1985 | |
| JP | H06344285 | 12/1994 | |
| JP | H8-280709 | 10/1996 | |
| JP | H10216238 | 8/1998 | |
| JP | 2003024336 | 1/2003 | |
| JP | 2007-325936 | 12/2007 | |
| WO | 9320535 | 10/1993 | |
| WO | 1996/039944 | 12/1996 | |
| WO | 9639944 | 12/1998 | |
| WO | 00/51486 A1 | 9/2000 | |
| WO | 2003049596 | 6/2003 | |
| WO | 2006/120666 | 11/2006 | |
| WO | 2007056590 | 5/2007 | |
| WO | 2007/088208 | 8/2007 | |
| WO | 2007/098494 | 8/2007 | |
| WO | 2007/120329 | 10/2007 | |
| WO | 2007136803 | 11/2007 | |
| WO | 2007/146325 | 12/2007 | |
| WO | 2007143859 | 12/2007 | |
| WO | 2008045831 | 4/2008 | |
| WO | 2008101228 | 8/2008 | |
| WO | 2008103212 | 8/2008 | |
| WO | WO-2008101228 A2 * | 8/2008 | ............ A61B 34/30 |
| WO | 2009/120982 | 10/2009 | |
| WO | 2009/120992 | 10/2009 | |
| WO | 2009120940 | 10/2009 | |
| WO | 2009120992 | 10/2009 | |
| WO | 2010025338 | 3/2010 | |
| WO | 2010059179 | 5/2010 | |
| WO | 2010068783 | 6/2010 | |
| WO | 2010107916 | 9/2010 | |

OTHER PUBLICATIONS

Title: International Search Report Citation: PCT Application No. PCT/US2011/030656 dated Jun. 13, 2011 8 pages.

Title: Emotiv—Brain Computer Interface Technology (online) Citation: <URL: http://www.emotiv.com> Publication Date: Aug. 11, 2011 3 pages.

Title: Supplemental European Search Report Citation: EP Application No. 09726364.4 dated Jan. 22, 2013 7 pages.

Title: Supplemental European Search Report Citation: EP Application No. 09723739.0 dated Jul. 10, 2012 6 pages.

Title: Supplemental European Search Report Citation: EP Application No. 09724550.0 dated Jul. 10, 2012 3 pages.

Title: International Search Report Citation: PCT Application No. PCT/US2009/058121 dated Nov. 19, 2009 2 pages.

Title: International Search Report Citation: PCT Application No. PCT/US2009/038536 dated May 28, 2009 2 pages.

Title: International Search Report Citation: PCT Application No. PCT/US2009/038534 dated May 27, 2009 2 pages.

Supplementary European Search Report for EP Application No. 11763410.5, dated Jun. 10, 2015. 7 pages.

Title: International Search Report Citation: PCT Application No. PCT/US2009/038597 dated May 18, 2009 2 pages.

(56) References Cited

OTHER PUBLICATIONS

Title: International Search Report Citation: PCT Application No. PCT/US2009/038618 dated May 22, 2009 2 pages.

An International Search Report for PCT Application No. PCT/US2009/069712, dated Feb. 25, 2010, 10 pgs.

A Supplementary European Search Report for EP Application No. 09725131.8, dated Feb. 20, 2013. 7 pgs.

Title: International Search Report Citation: PCT Application No. PCT/US2009/038525 dated May 27, 2009 2 pages.

Title: International Search Report Citation: PCT Application No. PCT/US2009/038531 dated May 19, 2009 3 pages.

Title: International Search Report Citation: PCT Application No. PCT/US2009/038533 dated Jun. 17, 2009 2 pages.

Title: The Aurora Electromagnetic Tracking System, Aurora Electromagnetic Measurement System—3D Tracking for Medical Guidance Citation: Northern Digital, Inc. <URL: http://www.ndigital.com/medical/aurora.pho?act=print> Publication Date: (actual publication date unknown) 3 pages.

Title: Apple Wins Strategic Multitouch and Music Tempo Workout Patents Citation: Patently Apple <URL: http://www.patentlyapple.com/patently-apple/2010/04/apple-wins-strategic-multitouch-music-tempo-workout-patents.html> Publication Date: (actual publication date unknown) 5 pages.

Polaris Family of Optical Tracking Systems, Polaris Vicra & Spectra—Optical Measurement Systems for Medical Citation: Northern Digital Inc. <URL: http://www.ndigital.com/medical/polarisfamily.php?act=print> Publication Date: (actual publication date unknown) 5 pages.

Author: LaBelle, Kathryn Title: Evaluation of Kinect Joint Tracking for Clinical and In-Home Stroke Rehabilitation Tools Citation: <http://netscale.cse.nd.edu/twiki/pub/Edu/KinectRehabilitation/Eval_of_Kinect_for_Rehab.pdf> Publication Date: Dec. 2011 67 pages.

Author: Padoy, Nicolas Title: Needle Insertion Revisted (telesurgery in depth), (online) Citation: The John Hopkins University <URL: http://www.youtube.com/watch?v=YsY_A0kLh-g> Publication Date: Jan. 2011 25 pages.

Title: Emotiv EPOC Software Development Kit—EPOC neuroheadset (online) Citation: <URL: http://www.emotiv.com/store/hardware/epoc/bci/epoc-neuroheadseU> Publication Date: (actual publication date unknown) 2 pages.

Title: Wii Remote—Wikipedia, the free encyclopedia (online) Citation: <URL: http://en.wikipedia.org/wiki/Wii_Remote> Publication Date: (actual publication date unknown) 17 pages.

Title: About the Kinect for Windows SDK—Microsoft Research (online) Citation: <URL: http://research.microsoft.com/en-us/um/redmond/projects/kinectsdk/about.aspx> Publication Date: (actual publication date unknown) 2 pages.

Title: Kinect—Wikipedia, the free encyclopedia (online) Citation: <URL: http://en.wikipedia.org/wiki/Kinect> Publication Date: (actual publication date unknown) 15 pages.

Title: International Search Report & Written Opinion Citation: PCT/US2012/031008 dated Jul. 20, 2012 10 pages.

Title: International Search Report and Written Opinion Cltation: PCT/US2011/030764 dated Aug. 15, 2011 8 pages.

Ghobadi, et al. "Real Time Hand Based Robot Control Using Multimodal Images", IAENG International Journal of Computer Sciences, 35:4, IJCS_35_4_08; Nov. 20, 2008. 6 pgs.

Robot.pdf (Robot—Definition Robot at Dictionary.com, Oct. 27, 2015, http://dictionary.reference.com/browse/robot, pp. 1-5).

* cited by examiner

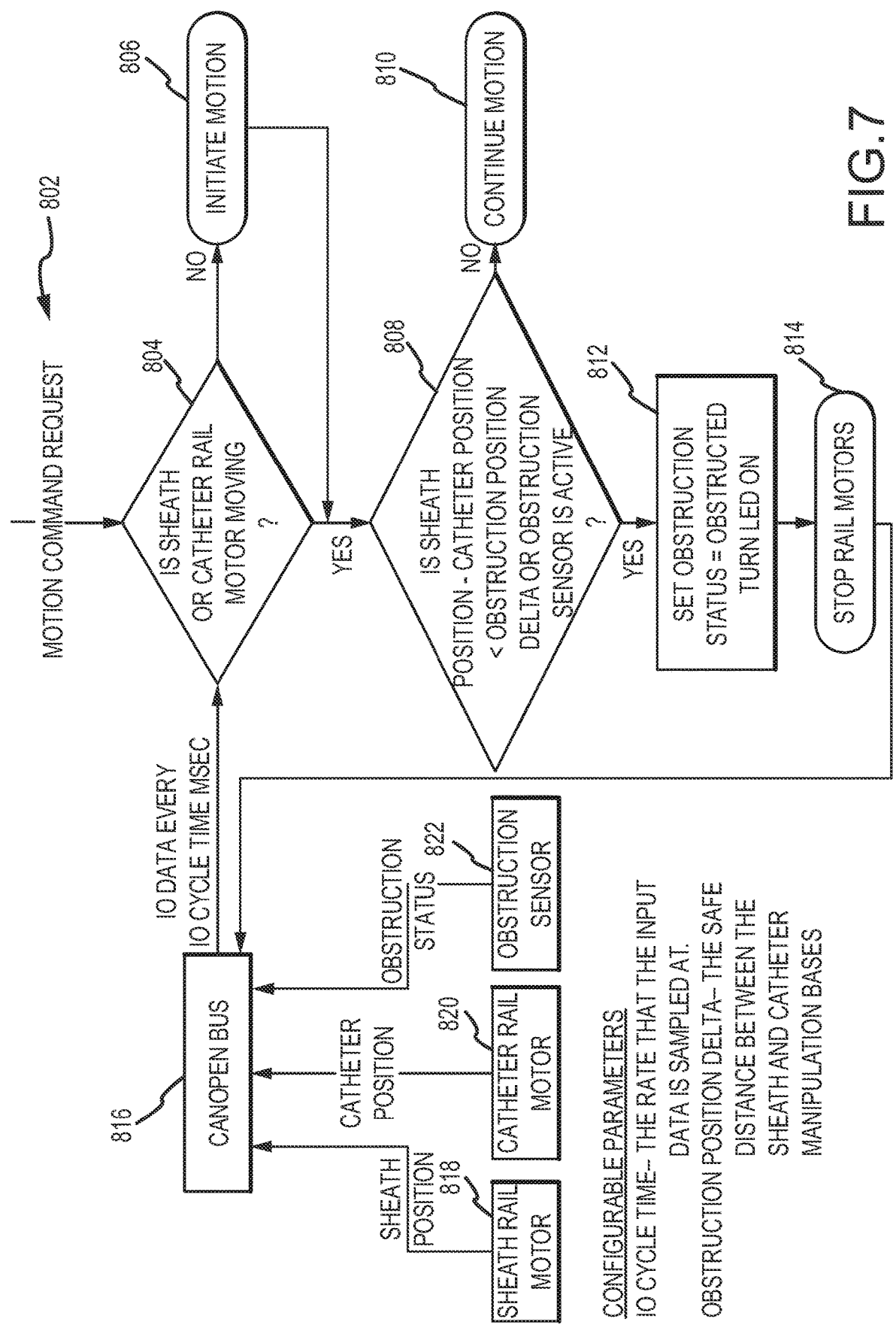

SYSTEM AND METHOD OF AUTOMATIC DETECTION OF OBSTRUCTIONS FOR A ROBOTIC CATHETER SYSTEM

CROSS REFERENCE TO RELATED APPLICATIONS

This application is a continuation of U.S. application Ser. No. 15/089,791 filed 4 Apr. 2016, and now U.S. Pat. No. 10,426,557, which is a continuation of U.S. application Ser. No. 13/120,715 filed 24 Mar. 2011 and now U.S. Pat. No. 9,301,810 which is a United States national stage filing based upon PCT Application No. PCT/US2009/058121 (the '121 application) filed 23 Sep. 2009, which claims priority to and is a continuation of United States non-provisional application Ser. No. 12/347,811, filed 31 Dec. 2008 (the '811 application) and now U.S. Pat. No. 8,343,096, Ser. No. 12/347,826, filed 31 Dec. 2008 (the '826 application) and now U.S. Pat. No. 8,317,744, Ser. No. 12/347,835, filed 31 Dec. 2008 (the '835 application) and now U.S. Pat. No. 8,684,962, Ser. No. 12/347,842, filed 31 Dec. 2008 (the '842 application) and now U.S. Pat. No. 8,317,745, each of which claim the benefit of U.S. provisional application No. 61/099,904, filed 24 Sep. 2008 (the '904 application). The '811 application, '826 application, '835 application, and '842 application, and, subsequently this application also claim the benefit of U.S. provisional application No. 61/040,143, filed 27 Mar. 2008 (the '143 application). The '121 application, '811 application, '826 application, '835 application, '842 application, '143 application, and '904 application are hereby incorporated by reference as though fully set forth herein.

BACKGROUND OF THE INVENTION a. Field of the Invention

This invention relates to a robotic catheter system and method for automated control of a catheter and related components. In particular, the instant invention relates to a robotic catheter system including a system and method for detection of obstructions that may hinder or otherwise stop movement of catheter and/or sheath manipulation bases, and related components during operation of the robotic catheter system.

b. Background Art

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other treatments. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to and at the treatment site, which can invariably be a function of a user's skill level.

One method of minimizing invariability due to a user's skill level involves the use of robotic catheter systems, such as the robotic catheter system described in detail in commonly owned and copending application Ser. No. 12/347,811 titled "Robotic Catheter System". As readily evident, such robotic catheter systems include a variety of safety concerns that must be addressed to prevent harm to a patient and the system operator. One such safety concern includes the possibility of an obstruction in the path of manipulation bases supporting the catheter and sheath cartridges, the layout and operation of which is also described in detail in the aforementioned "Robotic Catheter System" application.

The inventors herein have thus recognized the need for a system and method for detection of obstructions that may hinder or otherwise stop movement of manipulation bases and related components, and have further recognized the need for a system and method for controlling movement of the manipulation bases in a predetermined manner based on the type and location of an obstruction, and other factors involving movement of the manipulation bases.

BRIEF SUMMARY OF THE INVENTION

An obstruction detection system for a robotic catheter system may include a robotic catheter manipulator assembly including one or more catheter and sheath manipulation bases, with each manipulation base being generally linearly movable on one or more tracks relative to the robotic catheter manipulator assembly. The obstruction detection system may include one or more obstruction detection sensors disposed on the track and/or on the manipulation bases to detect an obstruction along a path of motion of the manipulation bases.

For the obstruction detection system described above, in one embodiment, the obstruction detection sensors may be ultrasonic sensors or light-emitting sensors. In one embodiment, the obstruction detection system may include obstruction detection sensors located at both ends of the track. In another embodiment, the obstruction detection system may include obstruction detection sensors located at both longitudinal ends of the catheter and sheath manipulation bases. In one embodiment of the obstruction detection system, the obstruction detection sensors enable maintenance of a predetermined distance between the catheter and sheath manipulation bases.

For the obstruction detection system described above, in one embodiment, the system may include a software system for monitoring movement of the catheter and sheath manipulation bases, and/or a sensor status of one or more obstruction detection sensors. In one embodiment of the obstruction detection system, the software system may include code for determining if a relative distance between the catheter and sheath manipulation bases is less than a predetermined distance; if the relative distance is less than the predetermined distance, then indicating an obstruction status of the catheter and sheath manipulation bases as obstructed, and stopping motion of the catheter and sheath manipulation bases, and if the relative distance is greater than or equal to the predetermined distance, then indicating the obstruction status of the catheter and sheath manipulation bases as unobstructed, and allowing motion of the catheter and sheath manipulation bases. In another embodiment, the obstruction detection system may include LEDs, visual signals, audible signals, and/or haptic feedback to a user input device, for indicating the obstruction status of the catheter and sheath manipulation bases.

For the obstruction detection system described above, in one embodiment, the system may include code for determining a relative distance between the catheter and sheath manipulation bases by determining an amount of rotation of motors that drive the catheter and sheath manipulation bases. In one embodiment of the obstruction detection system, the software system may include code for stopping motion of the catheter and sheath manipulation bases if the sensor status of the obstruction detection sensors is obstructed, and allowing motion of the catheter and sheath manipulation bases if the sensor status of all obstruction detection sensors is unobstructed.

For the obstruction detection system described above, in one embodiment, the system may include code for determining a direction of travel of the catheter and sheath manipulation bases, and allowing motion of the catheter and sheath manipulation bases if the sensor status of one of the obstruction detection sensors is obstructed, only if the direction of travel is away from the obstruction. In one embodiment of the obstruction detection system, the software system may include code for determining a direction of travel of the catheter and sheath manipulation bases by determining a direction of rotation of motors that drive the catheter and sheath manipulation bases.

For the obstruction detection system described above, in one embodiment, the system may include LEDs, visual signals, audible signals, and/or haptic feedback to a user input device, for indicating the sensor status of the obstruction detection sensor. In one embodiment of the obstruction detection system, the software system may monitor the manipulation bases and the obstruction detection sensors by means of a CANOpen protocol standard.

The invention also provides an obstruction detection system for a robotic catheter system including a robotic catheter manipulator assembly including one or more catheter manipulation bases and one or more sheath manipulation bases, with each manipulation base being generally linearly movable on one or more tracks relative to the robotic catheter manipulator assembly. The obstruction detection system may include detection means disposed on the track or on the manipulation bases to detect an obstruction along a path of motion of the manipulation bases, and monitoring means for monitoring movement of the catheter and sheath manipulation bases, and/or a detection status of the detection means.

For the obstruction detection system described above, in one embodiment, the detection means may be an ultrasonic sensor or a light-emitting sensor. In one embodiment of the obstruction detection system, the detection means may include obstruction detection sensors located at both ends of the track. In another embodiment of the obstruction detection system, the detection means may include obstruction detection sensors located at both longitudinal ends of the catheter and sheath manipulation bases. In one embodiment of the obstruction detection system, the obstruction detection sensors may enable maintenance of a predetermined distance between the catheter and sheath manipulation bases.

For the obstruction detection system described above, in one embodiment, the system may include monitoring means in the form of a software system including code for determining if a relative distance between the catheter and sheath manipulation bases is less than a predetermined distance; if the relative distance is less than the predetermined distance, then indicating an obstruction status of the catheter and sheath manipulation bases as obstructed, and stopping motion of the catheter and sheath manipulation bases, and if the relative distance is greater than or equal to the predetermined distance, then indicating the obstruction status of the catheter and sheath manipulation bases as unobstructed, and allowing motion of the catheter and sheath manipulation bases.

For the obstruction detection system described above, in one embodiment, the system may include means for indicating the obstruction status of the catheter and sheath manipulation bases. In one embodiment of the obstruction detection system, the means for indicating may include LEDs, visual signals, audible signals, and/or haptic feedback to a user input device.

For the obstruction detection system described above, in one embodiment, the system may include monitoring means in the form of a software system including code for determining a relative distance between the catheter and sheath manipulation bases by determining an amount of rotation of motors that drive the catheter and sheath manipulation bases.

For the obstruction detection system described above, in one embodiment, the system may include monitoring means in the form of a software system including code for stopping motion of the catheter and sheath manipulation bases if the detection status of the obstruction detection sensors is obstructed, and allowing motion of the catheter and sheath manipulation bases if the detection status of all obstruction detection sensors is unobstructed. In one embodiment of the obstruction detection system, the monitoring means may be a software system including code for determining a direction of travel of the catheter and sheath manipulation bases, and allowing motion of the catheter and sheath manipulation bases if the detection status of one of the obstruction detection sensors is obstructed, only if the direction of travel is away from the obstruction. In one embodiment of the obstruction detection system, the monitoring means may be a software system including code for determining a direction of travel of the catheter and sheath manipulation bases by determining a direction of rotation of motors that drive the catheter and sheath manipulation bases.

For the obstruction detection system described above, in one embodiment, the system may include means for indicating the detection status of the obstruction detection sensor. In one embodiment of the obstruction detection system, the means for indicating may include LEDs, visual signals, audible signals, and/or haptic feedback to a user input device. In one embodiment of the obstruction detection system, the monitoring means may monitor the manipulation bases and the detection means by means of a CANOpen protocol standard.

The foregoing and other aspects, features, details, utilities and advantages of the present invention will be apparent from reading the following description and claims, and from reviewing the accompanying drawings.

BRIEF DESCRIPTION OF THE DRAWINGS

FIG. 7 is a flow-chart of the control logic for the obstruction detection system according the invention.

DETAILED DESCRIPTION OF EMBODIMENTS OF THE INVENTION

Figure 1:
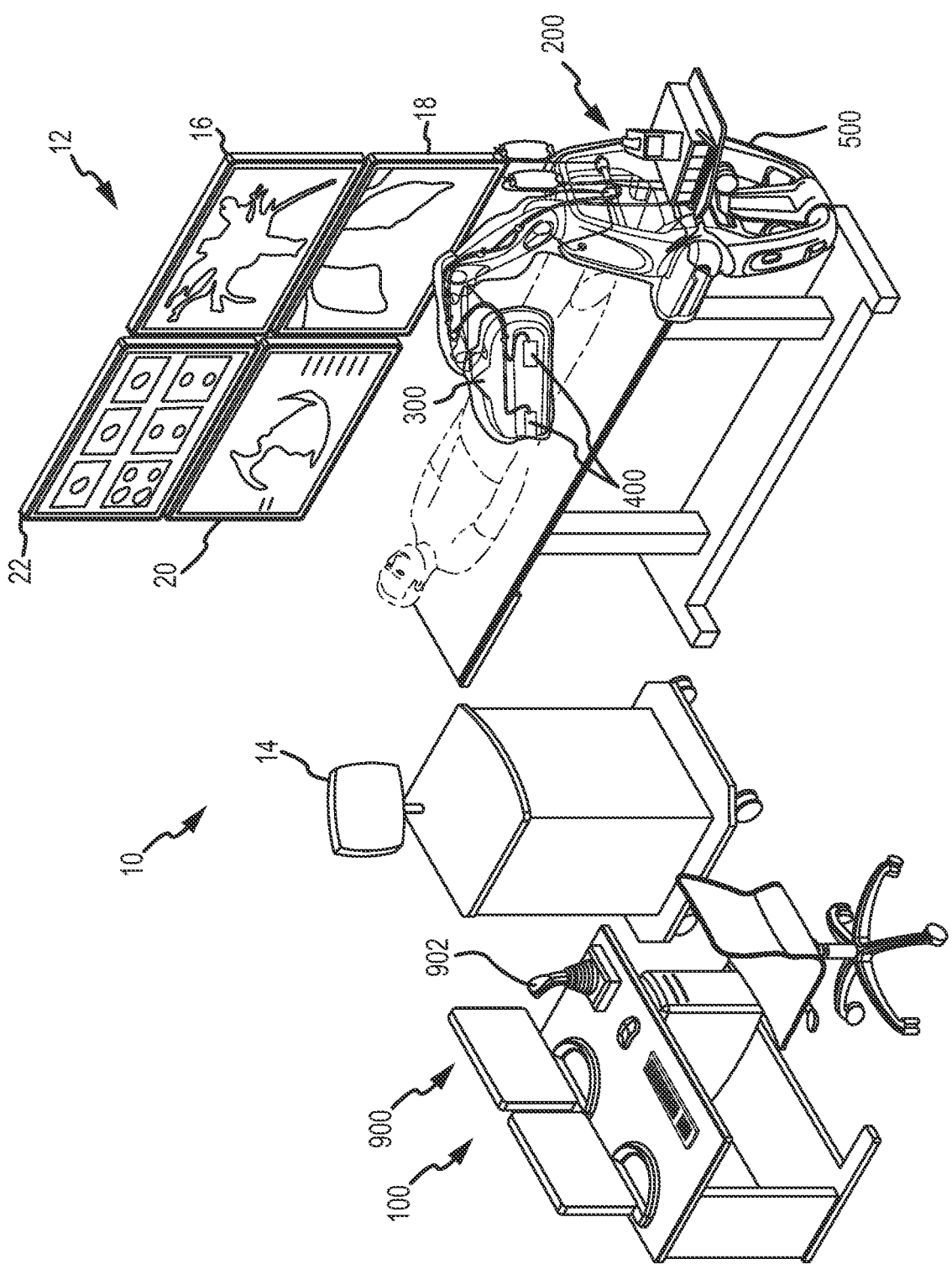
FIG. 1 is an isometric diagrammatic view of a robotic catheter system, illustrating an exemplary layout of various system components.

Referring now to the drawings wherein like reference numerals are used to identify identical components in the various views, an embodiment of robotic catheter system 10 (described in detail in commonly owned and copending application Ser. No. 12/347,811 titled "Robotic Catheter System"), also referred to as "the system," may be likened to "fly by wire" operation for a catheter system. The system may be used, for example, to manipulate the location and orientation of catheters and sheaths in a heart chamber or in another body cavity. As shown in FIG. 1, robotic catheter system 10 may generally incorporate a human input device and control system (referred to as "input control system") 100, e.g., a joystick and related controls (described briefly below and in detail in commonly owned and copending Application Serial No. PCT/US2009/038618 titled "Robotic Catheter System Input Device"), that a user such as an electrophysiologist (EP) may interact with, an electronic control system 200 (described briefly below and in detail in commonly owned and copending Application Serial No. PCT/US2009/038597 titled "Robotic Catheter System with Dynamic Response") that translates motions of the user at the input device into a resulting movement of a catheter tip, and a visualization system 12 that provides a user with real-time or near-real-time positioning information concerning the catheter tip. The system may further include closed-loop feedback using an EnSite NavX™ Navigation and Visualization system 14 and/or optical force transducers, a robotic catheter manipulator assembly 300 (described briefly below and in detail in commonly owned and copending application Ser. No. 12/347,826 titled "Robotic Catheter Manipulator Assembly") for operating a robotic catheter device cartridge 400 (described briefly below and in detail in commonly owned and copending application Ser. No. 12/347,835 titled "Robotic Catheter Device Cartridge" and application Ser. No. 12/347,842 "Robotic Catheter Rotatable Device Cartridge"), and manipulator support structure 500 (described briefly below and in detail in commonly owned and copending application Ser. No. 12/347,811 titled "Robotic Catheter System"). As discussed in detail below, robotic catheter system 10 may include an obstruction detection system 600 for detection of obstructions that may hinder or otherwise stop movement of catheter and sheath manipulation bases, and related components during operation of the robotic catheter system. The respective disclosures of the above-identified and other commonly owned and copending applications discussed in this application are incorporated herein by reference.

Before proceeding with a detailed description of obstruction detection system 600, the general layout and operation of the components of robotic catheter system 10 will be described with reference to FIGS. 1-5e to provide a basis for the operation of obstruction detection system 600.

An embodiment of robotic catheter system 10 may involve automated catheter movement. A user, such as an EP, could identify locations (potentially forming a path) on a rendered computer model of the cardiac anatomy. The system can be configured to relate those digitally selected points to positions within a patient's actual/physical anatomy, and may command and control the movement of a catheter to defined positions. Once in position, either the user or system could then perform the desired treatment or therapy—which may further be in accordance with a defined algorithm. This system could enable full robotic control by using optimized path planning routines together with closed-loop position control. Furthermore, the system could automate certain "best-practices," such as pulling the catheter across the surface, or making contact at an oblique angle.

Referring to FIG. 1, input control system 100, described below and in commonly owned and copending application titled "Robotic Catheter System Input Device," may generally allow a user to control the movement and advancement of both the catheter and sheath. Generally, several types of joysticks may be employed, including, without limitation, instrumented traditional catheter handle controls, oversized catheter models, instrumented, user-wearable gloves, and traditional joysticks. In embodiments, for example and without limitation, the joystick may be spring or motor centering so that any movement from the center position causes an incremental movement of the actual catheter tip, or the joystick may work in absolute terms.

Referring to FIG. 1, electronic control system 200 will be described briefly.

As discussed in detail in commonly owned and copending applications titled "Robotic Catheter System Input Device," and "Robotic Catheter System with Dynamic Response," many additional features may be included with embodiments of the system to, for example, improve the accuracy or effectiveness of the system. Such features may include, closed-loop feedback using EnSite NavX™ Navigation and Visualization system 14 for creating realistic cardiac chamber geometries or models, displaying activation timing and voltage data to identify arrhythmias, and guiding precise catheter movement, and/or optical force transducers; active tensioning of "passive" steering wires to reduce the system response time; cumulative ablation while the tip is following a front-to-back ironing motion; and/or reactive/resistive impedance monitoring.

Referring to FIG. 1, visualization system 12 will be described briefly.

Visualization system 12 may provide a user with real-time or near-real-time positioning information concerning the catheter tip. In an exemplary embodiment, system 12 may include an EnSite NavX™ Navigation and Visualization monitor 16 for displaying cardiac chamber geometries or models, displaying activation timing and voltage data to identify arrhythmias, and for facilitating guidance of catheter movement. A fluoroscopy monitor 18 may be provided for displaying a real-time x-ray image or for assisting a physician with catheter movement. Additional exemplary displays may include an ICE and EP Pruka displays, 20, 22, respectively.

Referring to FIG. 1, EnSite NavX™ Navigation and Visualization system 14 will be described briefly.

EnSite NavX™ Navigation and Visualization system 14 (described in detail in U.S. Pat. No. 7,263,397, titled "Method and Apparatus for Catheter Navigation and Location and Mapping in the Heart," incorporated by reference in its entirety) may be provided for creating realistic cardiac chamber geometries or models, displaying activation timing and voltage data to identify arrhythmias, and guiding precise catheter movement. System 14 may collect electrical data from catheters and use this information to track or navigate their movement and construct three-dimensional (3-D) models of the chamber.

Referring to FIGS. 1-5e, robotic catheter manipulator assembly 300 for operating robotic catheter device cartridges 400, various embodiments of which are described in detail in the aforementioned commonly owned and copending applications, will be described briefly for facilitating an understanding of input control system 100, and the operational integration of an haptic feedback system 900 with manipulator assembly 300 for controlling cartridges 400.

Figure 3A:
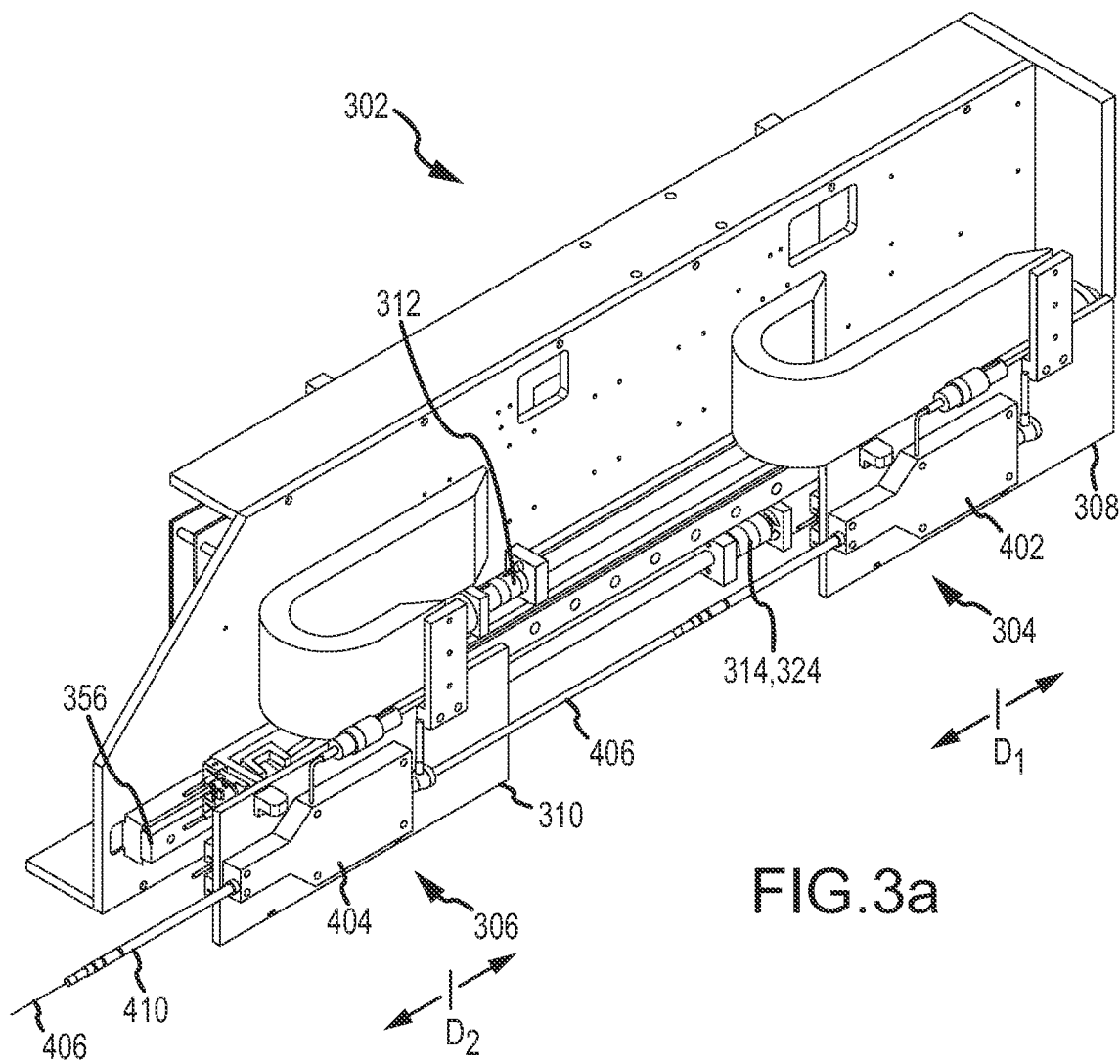
FIGS. 3a-3c are enlarged isometric views of an embodiment of a robotic catheter manipulator assembly.
Figure 3B:
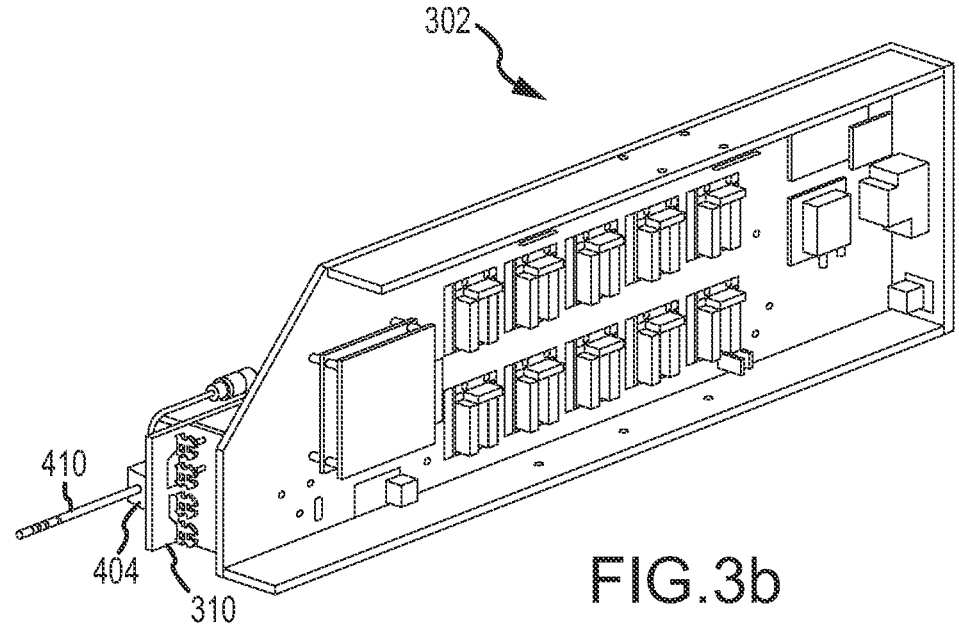
Figure 3C:
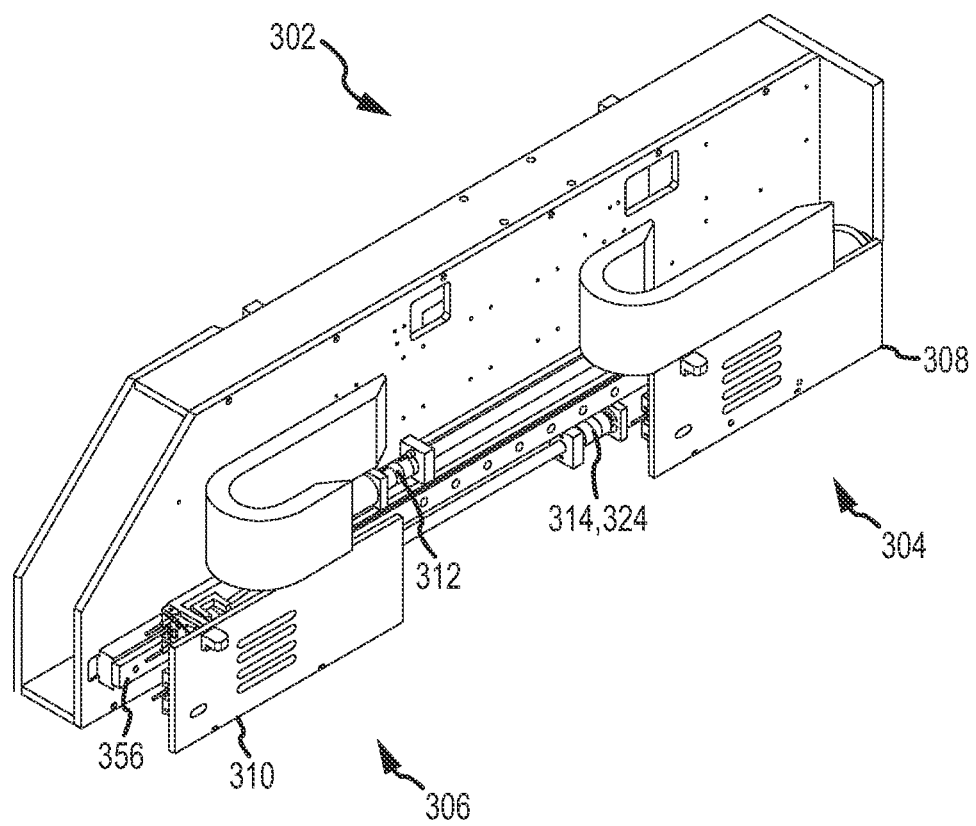
Figure 3E:
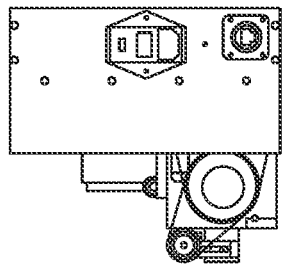
FIGS. 3d-3g are respectively enlarged left side, right side, top and front views of the robotic catheter manipulator assembly of FIG. 3a, illustrating use of the manipulator assembly with a robotic catheter rotatable device cartridge.
Figure 3F:
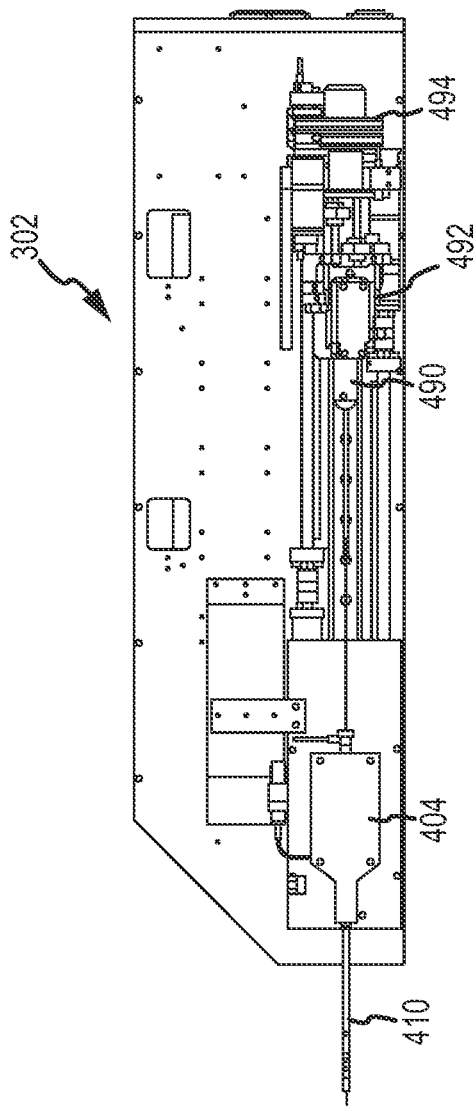
Figure 3D:
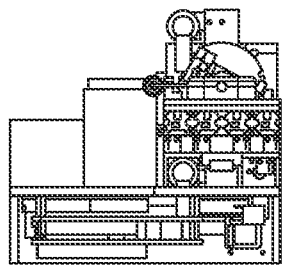

As generally shown in FIGS. 1 and 3a-5e, robotic catheter system 10 which includes one or more robotic catheter manipulator assemblies 300, includes an embodiment of robotic catheter manipulator assembly 302 including both catheter and sheath manipulation mechanisms 304, 306 for manipulating, for example, catheter and sheath cartridges 402, 404. Manipulator assembly 302 may include interconnected/interlocking manipulation bases 308, 310 for catheter and sheath cartridges 402, 404, and likewise may include electrical "handshake" functionality as discussed below. Each interlocking base 308, 310 may be capable of travel in the longitudinal direction of the catheter/sheath ($D_1$, $D_2$ respectively). In an embodiment, $D_1$ and $D_2$ may each represent a translation of approximately 8 linear inches. As shown in FIG. 3a, each interlocking base may be translated by high precision drive mechanisms 312, 314. Such drive mechanisms may include, for example and without limitation, a motor driven lead screw or ball screw.

As shown in FIGS. 3a-5e, for each cartridge 402, 404, an associated manipulation base 308, 310 may include a plurality of fingers 316, 318, 320 and 322, (e.g., one per steering wire) that extend or protrude upwardly to contact and interact with the steering wire slider blocks (such as slider blocks 412, 414, 416, 418) to independently tension select steering wires 420, 422, 424, 426. Each finger can be configured to be independently actuated by a precision drive mechanism, such as a motor driven ball screw 324, and may be outfitted with force sensors to measure corresponding steering wire tension. A distal steering wire encoder (not shown) may also be provided for force measurements at the distal end of the steering wires adjacent the catheter distal end. Each motor driven ball screw (for both finger control and cartridge translation control) may further include encoders to measure a relative and/or an absolute position of each element of the system. As shown in FIG. 4a, bearing 332 and coupler 330 of ball screw 324 may engage frame 340 of respective bases 308, 310 and a corresponding finger 316, 318, 320 or 322 may be mounted adjacent a strain gauge for measuring the corresponding steering wire tension.

Figure 4A:
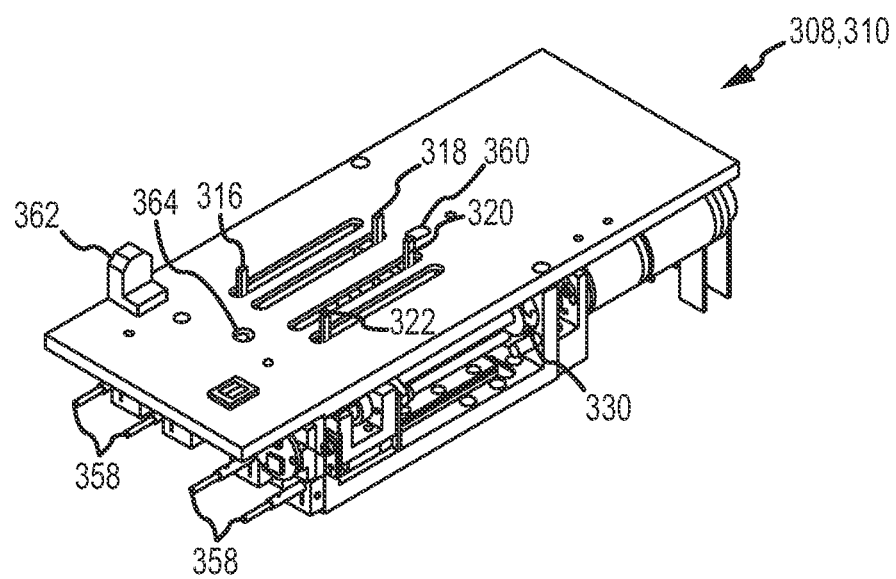
FIGS. 4a-4c are enlarged isometric views of an embodiment of a manipulation base.
Figure 4B:
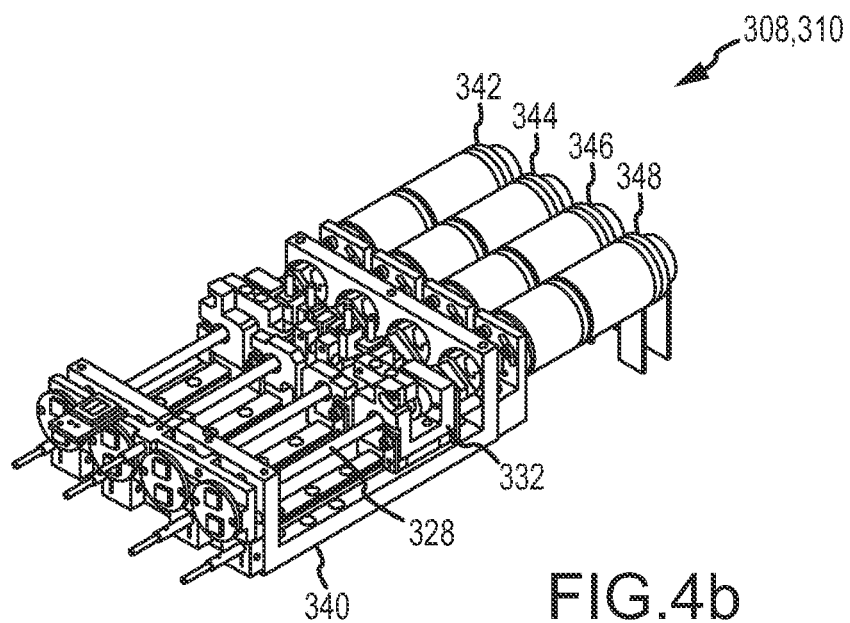
Figure 4C:
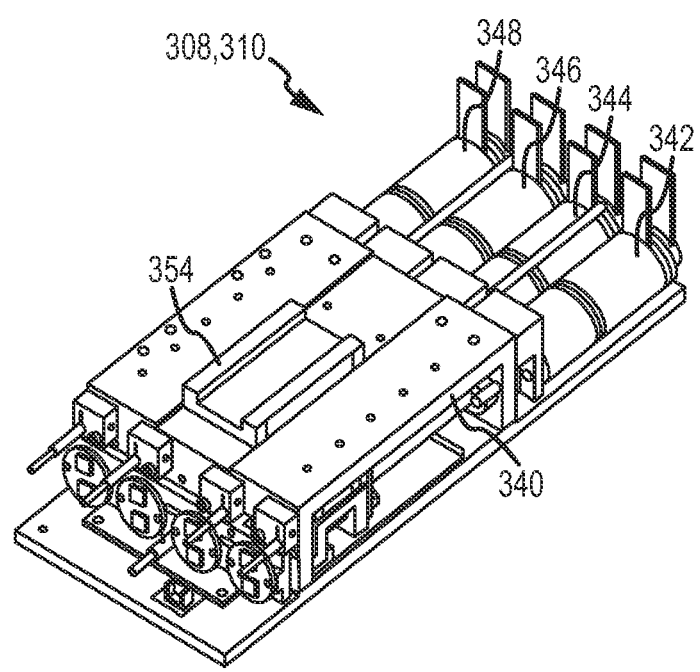

Referring to FIGS. 4a-4c, bases 308, 310 may include exemplary components such as motors 342, 344, 346 and 348, respectively coupled to fingers 316, 318, 320 and 322. A bearing 354 may be provided for sliding of bases 308, 310 on track 356. A plurality of inductive sensors (e.g. home sensors) 358 may be provided for guiding each manipulation base to a safe position.

Figure 2:
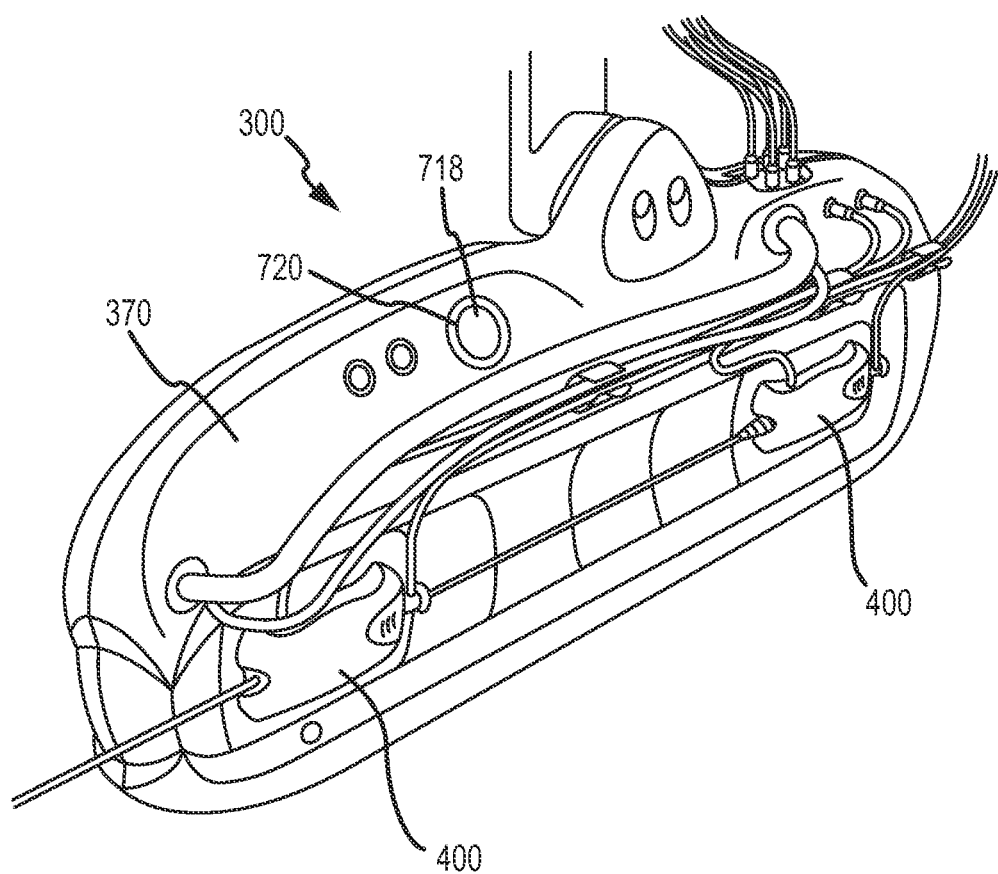
FIG. 2 is an enlarged isometric view of an exemplary robotic catheter manipulator assembly, also shown in FIG. 1.
Figure 3G:
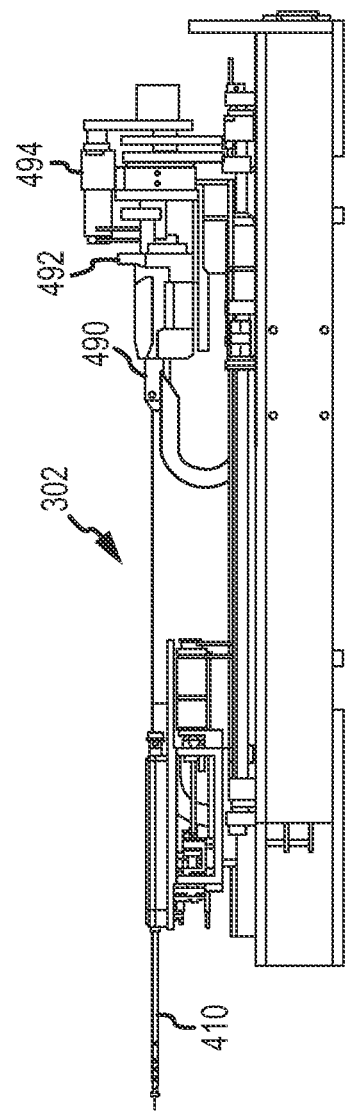

Referring to FIGS. 1-3g, particularly FIGS. 3d-3g, robotic catheter manipulator assembly 302 may be usable with a robotic catheter rotatable device cartridge 490, described in detail in commonly owned and copending application titled "Robotic Catheter Rotatable Device Cartridge." As shown in FIG. 3g, manipulator base 308 may be replaced with a robotic catheter rotatable drive head 492 and a robotic catheter rotatable drive mechanism 494, described in detail in commonly owned and copending application titled "Robotic Catheter Rotatable Drive Mechanism."

Referring to FIGS. 1 and 5a-5e, an embodiment of catheter and sheath cartridges 402, 404 will be described in detail.

As briefly discussed above, robotic catheter system 10 may include one or more cartridges 400, with manipulator 302 including at least two cartridges 402, 404, each of which may be respectively designed to control the distal movement of either the catheter or the sheath. With respect to catheter cartridge 402, catheter 406 may be substantially connected or affixed to cartridge 402, so that advancement of cartridge 402 correspondingly advances catheter 406, and retraction of the cartridge retracts the catheter. As further shown in FIGS. 5a-5e and discussed above, in an embodiment, each cartridge 402, 404 may include slider blocks (e.g., 412, 414, 416, 418), each rigidly (and independently) connected or affixed to one of a plurality of catheter steering wires (e.g., 420, 422, 424, 426) in a manner that permits independent tensioning of each steering wire. The cartridge may be provided as a disposable item that is capable of being easily positioned (e.g., snapped) into place in an overall assembly. In an embodiment, as discussed in detail below, the cartridge may include an electrical "handshake" device or component to allow the system to properly identify the cartridge (e.g., by type and/or proper placement/positioning). Sheath cartridge 404 may be designed in a similar manner as the catheter cartridge 402, but will typically be configured to provide for the passage of catheter 406. Assembly 302 may include a plurality (e.g., as many as ten or more) of independent driving mechanisms (e.g. motor driven ball screws 324).

For some embodiments, the catheter and sheath cartridge can be designed to be substantially similar, and in that context a reference to either may relate to both. For example, as shown in FIGS. 5a-5e, the design of the catheter/sheath cartridge may include upper and lower cartridge sections 428, 430, and independent slider blocks 412, 414, 416, 418. The system is not generally limited to specific material selection or formation techniques. However, in an embodiment, the upper and lower cartridge sections 428, 430 may be injection molded using a polycarbonate material. Each slider block 412, 414, 416, 418 may be connected to a separate catheter steering wire 420, 422, 424, 426, and may be formed of a Teflon-like material such as, for example, Delrin AF. When in contact with the cartridge housing portions 428, 430, such Teflon-like slider blocks may maintain a low static and dynamic coefficient of friction and may avoid the need for additional lubrication.

Figure 5A:
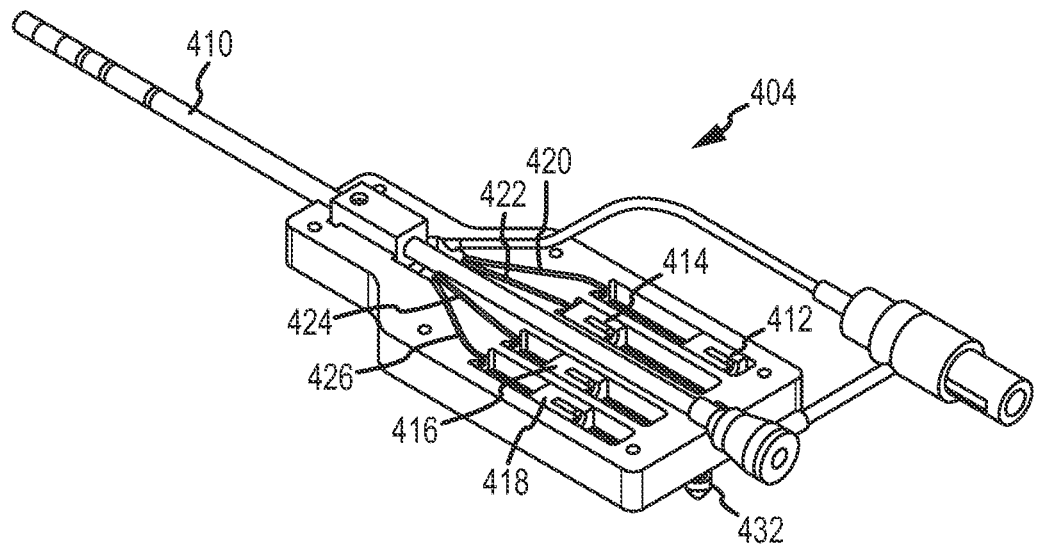
FIGS. 5a-5e are enlarged isometric views of an embodiment of a robotic catheter device cartridge, with FIG. 3a illustrating an exemplary usage of the robotic catheter device cartridge.
Figure 5B:
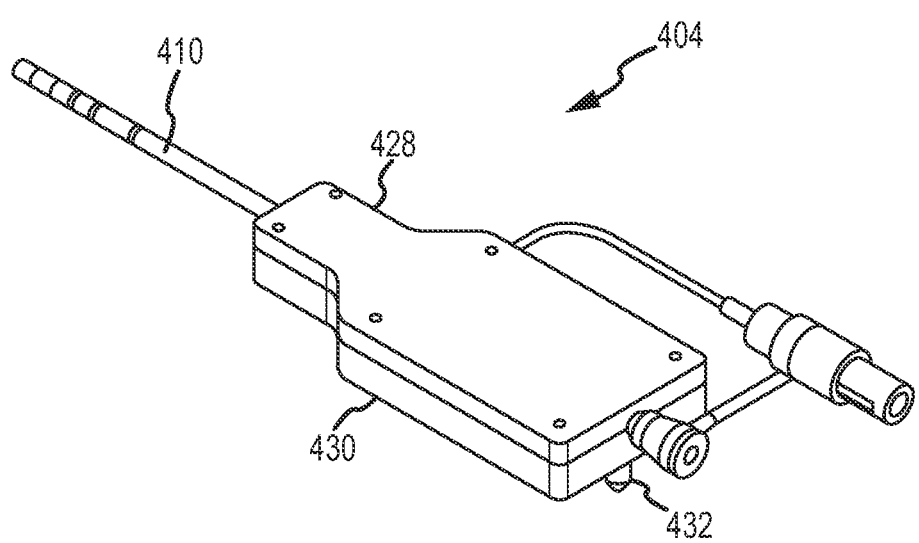
Figure 5C:
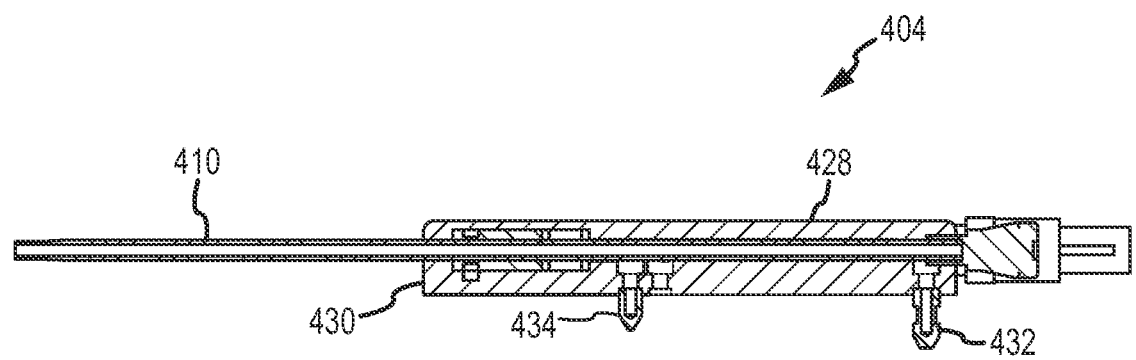
Figure 5D:
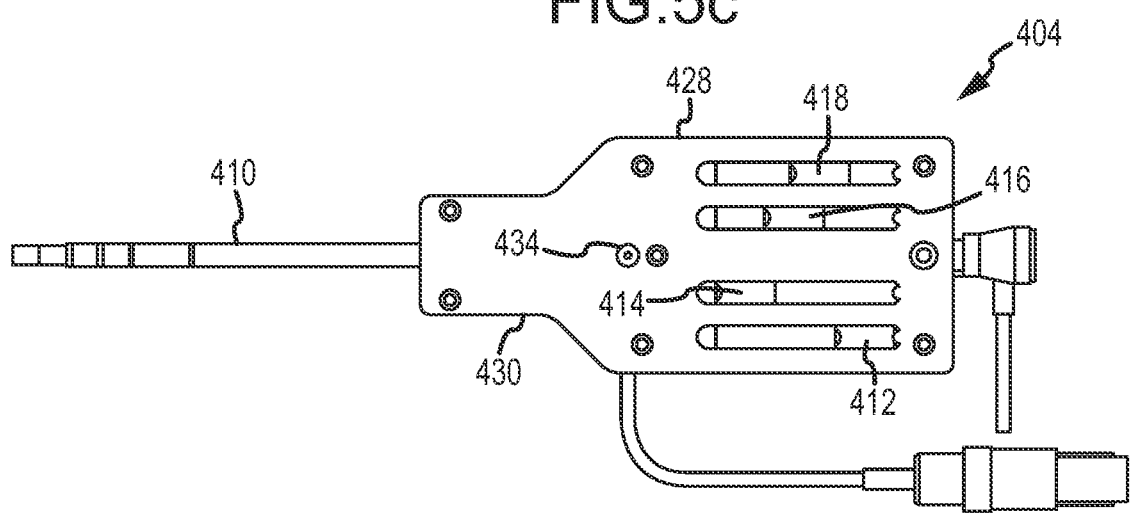
Figure 5E:
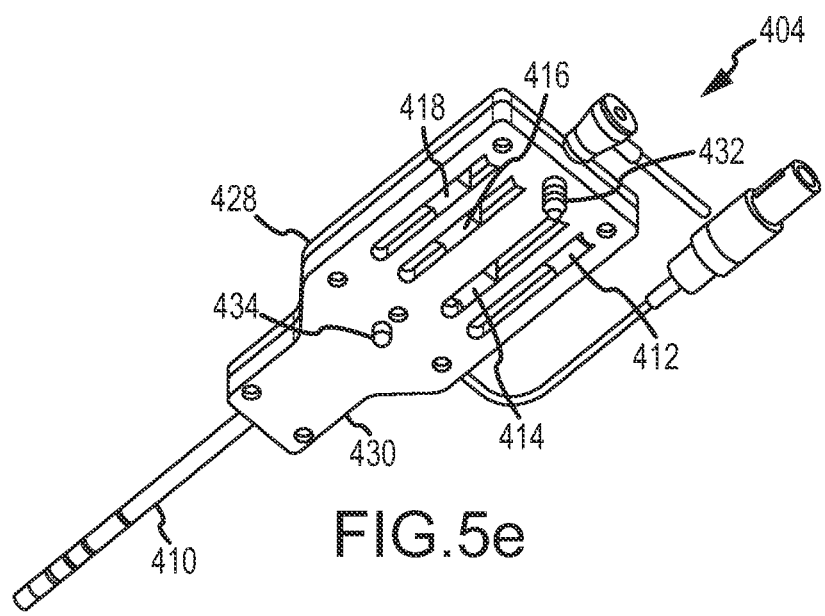

Referring to FIGS. 3a-5e and as discussed above, catheter and sheath cartridges 402, 404 may be configured to secure or lock down onto respective interconnecting catheter and sheath manipulation bases 308, 310. To couple cartridge 402 (and 404) with base 308 (and 310), one or more locking pins (e.g., 432 in FIGS. 5a, 5d and 5e) on the cartridge may engage one or more mating recesses 360 in the base (see FIG. 4a). In an embodiment, such recesses 360 may include an interference lock such as a spring detent or other locking means. In an embodiment, such other locking means may include a physical interference that may require affirmative/positive action by the user to release the cartridge. Such action may include or require actuation of a release lever 362. Additionally, as shown in FIGS. 5c, 5d and 5e, cartridge 402 (and 404) may include one or more locator pins 434 that are configured to passively fit into mating holes on the base (e.g., 364 in FIG. 4a).

In an embodiment, a user (e.g. an EP) may first manually position catheter 406 and sheath 410 (with catheter 406 inserted in sheath 410) within the vasculature of a patient. Once the devices are roughly positioned in relation to the heart, the user may then engage or connect (e.g., "snap-in") the catheter cartridge into place on interconnecting/interlocking bases 308, 310 of manipulator assembly 302, for example, by inserting the locking/locating pins 432, 434 of the cartridges into mating holes 360, 364 of respective base 308, 310. When the cartridge is interconnected with the base, each of the plurality of fingers 316, 318, 320 or 322 may fit into recesses formed between the distal edge of slider blocks 412, 414, 416, 418 and a lower portion of the cartridge housing. Such recesses are shown in, for example, FIGS. 5d and 5e. With sufficiently rigid coupling between each slider block and a corresponding steering wire, pushing a slider block in a proximal direction may cause an attached steering wire to tension and thus laterally deflect the distal end of the catheter and sheath 406, 410.

The aforementioned electrical handshake between manipulation bases 308, 310 and catheter and sheath cartridges 402, 404 will be described briefly.

Robotic catheter system 10 may be useful for a variety of procedures and in connection with a variety of tools and/or catheters. Such tools and/or catheters may include, without limitation, spiral catheters, ablation catheters, mapping catheters, balloon catheters, needle/dilator tools, cutting tools, cauterizing tools, and/or gripping tools. The system may additionally include a means of identifying the nature and/or type of catheter/tool cartridge that is installed for use, and/or position or connection related information. The system may automatically access/obtain additional information about the cartridge, such as, without limitation, its creation date, serial number, sterilization date, prior uses, etc.

Further, some embodiments of the system may include an ability to "read" or detect the type or nature of the connected cartridge through the use of memory included with the disposable cartridge together with some data/signal transmission means. By way of example, each cartridge may contain a chip (e.g., an EEPROM chip) that can be electrically interfaced by the manipulator head. Such a chip could, for instance, be programmed during the manufacturing process and may electronically store various data, such as the make; model; serial number; creation date; and/or other special features associated with the cartridge or tool. Additionally the chip may contain other worthwhile information, such as an indication of previous use, catheter specific calibration data, and/or any other information that may relate to the safety or performance of the particular device.

In an embodiment, upon interconnecting the cartridge (e.g. 402, 404) with the manipulator head (e.g. 302), a detection means, such as an optical or magnetic sensor, may initially detect the presence of the cartridge. Once presence is detected, the manipulator may energize a chip and initiate data/signal retrieval. Such retrieved data/signal may then be used by the system to control or alter various features and/or displays based on the type of device and/or information provided. While one embodiment may use a chip (e.g., EEPROM), due to its design flexibility, another embodiment may include a wireless transmission device, such as an RFID, which may be employed to facilitate the data storage/transfer instead of, or in addition to a chip.

Figure 6:
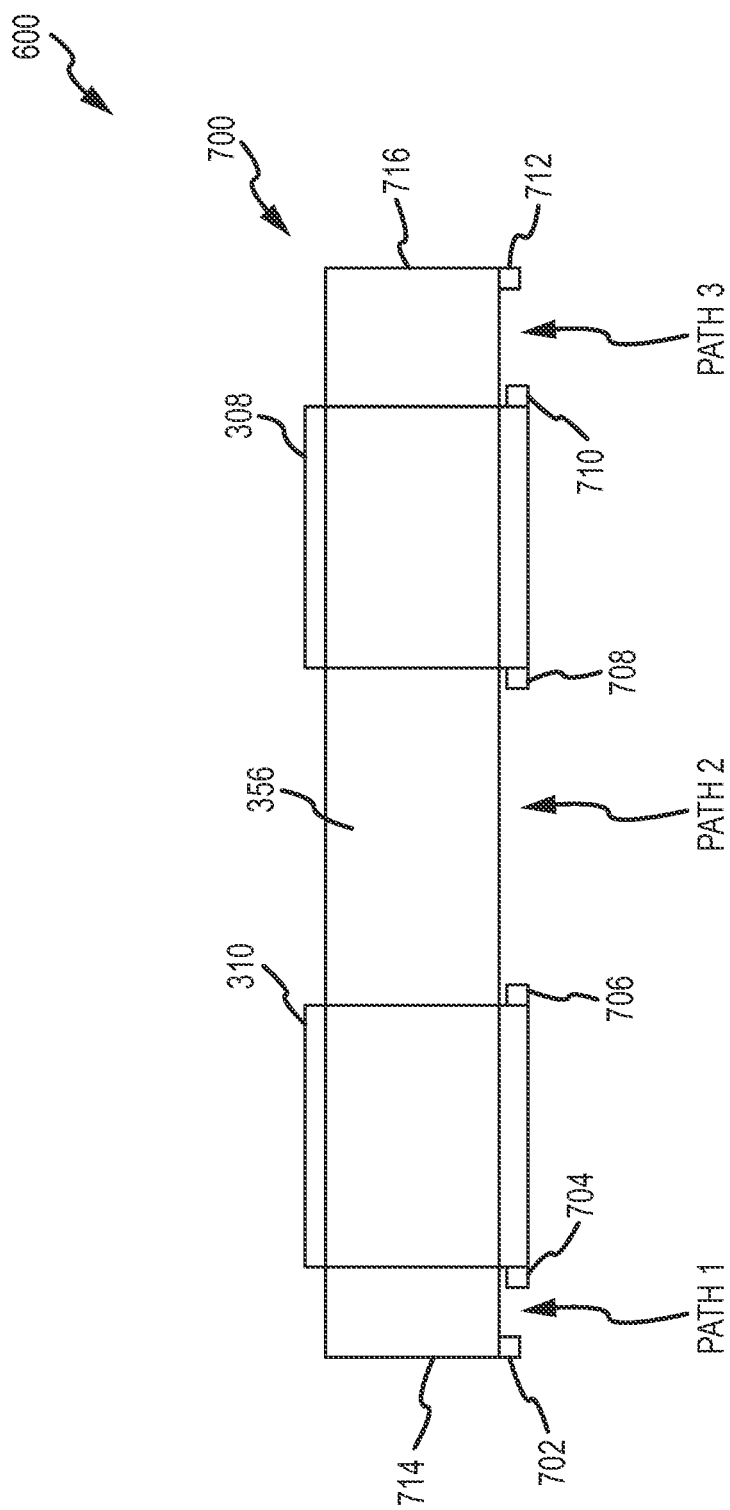
FIG. 6 is a sketch illustrative of exemplary placement of obstruction detection sensors for the obstruction detection system according to the invention.

Referring now to FIGS. 1-7, and particularly FIGS. 6 and 7, obstruction detection system 600 of the invention will be described in detail, and may generally include a hardware system 700 and a software system 800.

Referring to FIG. 6, hardware system 700 may include a plurality of obstruction detection sensors 702, 704, 706, 708, 710 and 712 (described in detail below) generally operatively interconnected with software system 800 for enabling, disabling or otherwise controlling movement of manipulation bases 308, 310. Obstruction detection system 600 may initiate control, or otherwise disable movement of manipulation bases 308, 310 as the bases generally move towards or away from each other on track 356 based on the particular nature of the operation being performed by a physician during surgery or by a technician, for example, during maintenance, or by a physician or technician during attachment or detachment of cartridges 402, 404. Since manipulator assembly 302 generally includes an enclosure 370 as shown in FIG. 2 partially or fully covering manipulation bases 308, 310, during typical operation, the general working area of manipulation bases 308, 310 remains covered. However, in the event of an obstruction being present in the path of manipulation bases 308, 310 or during routine maintenance of manipulator assembly 302 where a technician or operator may insert an object or finger in the area of manipulation bases 308, 310, enclosure 370 may be removed for access to manipulation bases 308, 310. The combination of hardware system 700 and a software system 800, as discussed herein, may detect the presence of an obstruction in the path of manipulation bases 308, 310 and stop movement of bases 308, 310 when certain criteria have been met.

In further detail, as shown in FIGS. 3a and 6, hardware system 700 may generally include obstruction detection sensors 702, 704, 706, 708, 710 and 712 respectively disposed on or along track 356 and manipulation bases 308, 310. In a particular embodiment of the invention, sensors 702-712 may be ultrasonic sensors, or alternatively, light-emitting sensors for detecting the presence of an obstruction. Sensors 702 and 712 may be disposed at the opposing ends of track 356, and sensors 704, 706, and 708, 710 may be respectively disposed at the corners or other suitable locations on manipulation bases 310, 308. Sensors 702, 704 may monitor the presence of any obstructions along Path 1 between manipulation base 310 and end 714 of track 356. Sensors 706, 708 may monitor the presence of any obstructions along Path 2 between manipulation bases 310 and 308, and sensors 710, 712 may monitor the presence of any obstructions along Path 3 between manipulation base 308 and end 716 of track 356. As discussed below, any positive (e.g. toward end 714) and negative (e.g. toward end 716) translation of manipulation base 308, 310 would be stopped in case of an obstruction along track 356.

Referring to FIG. 7, software system 800 operates in combination with hardware system 700 to track motion of manipulation bases 308, 310 on track 356, and more specifically, whether the manipulation bases are moving in a positive or negative direction, and their distance from each other. Typically, manipulation bases 308, 310 are designed to move within 2-3 millimeters of each other to prevent collision. Software system 800 may selectively activate one or more of sensors 702-712 upon actuation or movement of manipulation bases 308, 310 in a predetermined direction to detect any obstructions in the path of translation of a specific manipulation base. Alternatively, all sensors 702-712 may be activated so that software system 800 determines a proper course of action based on the location of an obstruction (e.g. along Path 1, Path 2 or Path 3), and other factors such as the direction of movement of the manipulation bases, and the actual function being performed (e.g. surgery or routine maintenance). Based on the specific function being performed, software system 800 may stop movement of the manipulation bases (e.g. by cutting power to high precision drive mechanisms 312, 314), allow movement of the manipulation bases, or reverse movement of the manipulation bases.

For example, if an obstruction is present along Path 2 and routine maintenance is being performed on manipulator assembly 302, software system 800 may stop movement of manipulation bases 308, 310 if they are moving toward each other, but can allow movement of the manipulation bases if they are moving away from each other. In this manner, if an obstruction (e.g. a hand or finger of a service technician) is present along Path 2, movement of the manipulation bases may only be halted if the bases are moving towards each other (e.g. to prevent contact with an obstruction), but may be otherwise allowed to continue. If the obstructions is present along Path 2, in a routine maintenance mode, manipulation bases 308, 310 may be directed to move away from each other such that a predetermined distance (e.g. 20 mm) remains between the bases for insertion of a technician's fingers or another object along Path 2 for maintenance operations.

One method of detecting motion of manipulation bases 308, 310 may be to detect the direction of motion of high precision drive mechanisms 312, 314, which operate via the CANOpen protocol standard. Referring to FIG. 7, the algorithm for software system 800 is illustrated and may include a motion command request at location 802 for initiating or continuing motion of manipulation bases 308, 310. At location 804, software system 800 may determine if high precision drive mechanisms 312, 314 are moving, and if not, motion may be initiated at location 806. At location 808, if high precision drive mechanisms 312, 314 are moving at step 804 or motion is initiated at step 806, then system 800 may determine if the position of the sheath manipulation base 310 minus the position of the catheter manipulation base 308 is less than a predetermined obstruction position delta (e.g. a predetermined safe distance between the sheath and catheter drive mechanisms; 20 mm in the example discussed above). Alternatively, at location 808, the system may also determine if any of the obstruction detection sensors 702-712 have been activated. If the determination at location 808 is no, then motion may continue at location 810. If the determination at location 808 is yes, then at location 812, system 800 may set an Obstruction Status flag to Obstructed, and turn LED 718 to red, as discussed in detail below with reference to FIG. 2. Thereafter at location 814, high precision drive mechanisms 312, 314 may be stopped by turning the power off or by other means. The off status of high precision drive mechanisms 312, 314 may then be fed to CANOpen protocol 816 for further evaluation. Once the Obstruction Status flag is cleared (e.g. no obstruction), LED 718 may be turned to green, as also discussed below.

The LED will be turned off as soon as the obstruction status flag is cleared.

In a particular embodiment, software system 800 may monitor high precision drive mechanisms 312, 314, for example, every 50 ms to determine the direction of movement and location of manipulation bases 308, 310 (e.g. location along track 356, and relative location). Software system 800 may thus monitor manipulation bases 308, 310, which operate via the CANOpen protocol standard, and further monitor the presence of any obstruction along Paths 1-3 as detected by sensors 702-712. Upon the detection of an obstruction, software system 800 may issue instructions through the CANOpen protocol to stop high precision drive mechanisms 312, 314, and thus manipulation bases 308, 310.

Thus, referring again to FIG. 7, at location 816, CANOpen protocol may receive input from locations 810, 820 and 822, which are respectively, monitors for sheath high precision drive mechanism 314, catheter high precision drive mechanism 312, and obstruction sensors 702-712. The data from the respective locations 810, 820 and 822 may be sampled at a predetermined rate (e.g. 50 ms) and fed into location 804 to determine movement of the catheter/sheath high precision drive mechanisms, and further evaluation as discussed above.

The combination of hardware system 700 including obstruction detection sensors 702-712, and software system 800 which monitors sensors 702-712 and high precision drive mechanisms 312, 314 operable via the CANOpen protocol standard, provides for an obstruction detection system 600 that monitors for obstructions along Paths 1-3 and stops motion of manipulation bases 308, 310 depending on factors such as the position of an obstruction, the direction of travel of the manipulation bases, and the type of operation being performed (e.g. surgery, routine maintenance, or cartridge replacement). Yet further, depending on the extent and location of an obstruction, system 600 may cut off power to all high precision drive mechanisms (e.g. 312, 314, 342, 344, 346 and 348; see FIGS. 3a and 4b), or just selective drive mechanisms depending on whether the obstruction is detected during surgery or maintenance. During surgery, this selective disablement of certain high precision drive mechanisms would allow critical functions to be performed, without entire system shut-down.

Referring to FIG. 2, a LED 718 may be provided for conveying the operational status of robotic catheter system 10 to a user. In a particular embodiment, LED 718 may include, for example, three light color indicators such as red, yellow, green for respectively indicating the requirement for system shutdown, a problem and the requirement for system maintenance, or proper system operation. Alternatively, LED 718 may include codes via, for example, blinks to indicate the type of problem. An emergency on/off switch 720 may also be provided to manually shut robotic catheter system 10 off in the event of an emergency, and as a redundant measure for shutting down system 10 and motion of manipulation bases 308, 310.

With the addition of obstruction detection system 600 to robotic catheter system 10, set-point calibration can be fully automated with the presence of obstruction detection sensors 702-712. Set-point calibration assures that when catheter and sheath cartridges 402, 404 are in place, there is a minimum amount of tension on steering wires 420, 422, 424 and 426 to enable control of the catheter/sheath. For example, in order to automate movement of catheter and sheath 406, 410, and set-point calibration during system initialization, system 600 may prevent movement of manipulation bases 308, 310 if an obstruction is detected along Paths 1-3. Specifically, once catheter and sheath cartridges 402, 404 are snapped onto manipulation bases 308, 310, if an obstruction is detected along Paths 1-3 by obstruction detection sensors 702-712, set-point calibration would not initiate until the user clears the obstruction. Such functionality would enhance the EP experience by providing additional safety for the robotic catheter system, and would also provide safety to a patient so that the desired movement of the sheath and catheter can be achieved without any obstruction. Additionally, obstruction detection system 600 may be include other visible or audible signals, and/or be integrated with haptic feedback system 900 so that when an obstruction is detected, haptic feedback is provided to a user via input control system 100 to stop further motion of the manipulation bases 308, 310, as well as catheter and sheath cartridges 402, 404, as needed.

The invention thus provides an obstruction detection system 600 for detection of obstructions that may hinder or otherwise stop movement of manipulation bases 308, 310, and related components. As discussed above, hardware system 700 and software system 800 of obstruction detection system 600 may operate in a cohesive manner to control movement of the manipulation bases in a predetermined manner based on the type and location of an obstruction, and other factors involving direction of movement of the manipulation bases.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. An obstruction detection system for a robotic catheter system including a robotic catheter manipulator assembly including at least one catheter manipulation base and at least one sheath manipulation base, each manipulation base being generally movable with respect to each other, the obstruction detection system comprising:
    an electronic control system configured to control movement of the at least one catheter manipulation base and the at least one sheath manipulation base and to receive a signal indicating information relating to the at least one catheter manipulation base and the at least one sheath manipulation base;
    wherein the electronic control system is configured to determine a relative distance between the at least one catheter manipulation base and the at least one sheath manipulation base and further configured to determine if the relative distance between the catheter and sheath manipulation bases is less than a predetermined distance, wherein if the relative distance is less than the predetermined distance, then the electronic control system indicates an obstruction status of the catheter and sheath manipulation bases as obstructed, and stopping motion of the catheter and sheath manipulation bases, wherein if the relative distance is greater than or equal to the predetermined distance, then the electronic control system indicates the obstruction status of the catheter and sheath manipulation bases as unobstructed, and allowing motion of the catheter and sheath manipulation bases.

2. The obstruction detection system according to claim 1, wherein the electronic control system is configured to keep the relative distance of the at least one catheter manipulation base and the at least one sheath manipulation base greater than a predetermined distance.

3. The obstruction detection system according to claim 1, wherein the at least one catheter manipulation base and the at least one sheath manipulation base are configured to be generally linearly movable in relation to each other.

4. The obstruction detection system according to claim 1, wherein the electronic control system is configured to maintain a predetermined distance between the at least one catheter and the at least one sheath manipulation bases.

5. The obstruction detection system according to claim 1, further comprising at least one of a light-emitting diode (LED), a visual signal, an audible signal, and haptic feedback to a user input device, for indicating the obstruction status of the at least one catheter and the at least one sheath manipulation bases.

6. The obstruction detection system according to claim 1, wherein the electronic control system:
    determines the relative distance between the at least one catheter and the at least one sheath manipulation bases by determining an amount of rotation of motors that drive the at least one catheter and the at least one sheath manipulation bases.

7. The obstruction detection system according to claim 1, wherein the electronic control system:
    determines a direction of travel of the at least one catheter and the at least one sheath manipulation bases by determining a direction of rotation of motors that drive at least one of the at least one catheter and the at least one sheath manipulation bases.

8. The obstruction detection system according to claim 1, wherein the electronic control system monitors the at least one manipulation bases by means of a CAN Open protocol standard.

9. An obstruction detection system for a robotic catheter system including a robotic catheter manipulator assembly including at least one catheter manipulation base and at least one sheath manipulation base, each manipulation base being generally movable with respect to each other, the obstruction detection system comprising:
    monitoring means for monitoring movement of the at least one catheter manipulation base and at least one sheath manipulation base,
    wherein the monitoring means is configured to move the at least one catheter manipulation base and the at least one sheath manipulation base; and
    wherein the monitoring means is configured to determine a relative distance between the at least one catheter manipulation base and the at least one sheath manipulation base, and wherein the monitoring means is further configured to determine if the relative distance between the catheter and sheath manipulation bases is less than a predetermined distance, wherein if the relative distance is less than the predetermined distance, then indicating an obstruction status of the catheter and sheath manipulation bases as obstructed, and stopping motion of the catheter and sheath manipulation bases, wherein if the relative distance is greater than or equal to the predetermined distance, then indicating the obstruction status of the catheter and sheath manipulation bases as unobstructed, and allowing motion of the catheter and sheath manipulation bases.

10. The obstruction detection system according to claim 9, wherein the at least one catheter manipulation base and the at least one sheath manipulation base are configured to be generally linearly movable in relation to each other.

11. The obstruction detection system according to claim 9, wherein the monitoring means acts to maintain a predetermined distance between the at least one catheter manipulation base and at least one sheath manipulation base.

12. The obstruction detection system according to claim 9, further comprising means for indicating the obstruction status of the at least one catheter and the at least one sheath manipulation bases.

13. The obstruction detection system according to claim 12, wherein the means for indicating is at least one of a light emitting diode (LED), a visual signal, an audible signal, and haptic feedback to a user input device.

14. The obstruction detection system according to claim 9, wherein an electronic control system is configured to cut power to the at least one catheter manipulation base and the at least one sheath manipulation base if the obstruction status of the at least one catheter and the at least one sheath manipulation bases shows as obstructed.

15. The obstruction detection system according to claim 9, wherein the monitoring means:
determines the relative distance between the at least one catheter and the at least one sheath manipulation bases by determining an amount of rotation of motors that drive the at least one catheter and the at least one sheath manipulation bases.

16. The obstruction detection system according to claim 9, wherein an electronic control system:
determines a direction of travel of the at least one catheter and the at least one sheath manipulation bases by determining a direction of rotation of motors that drive at least one of the at least one catheter and the at least one sheath manipulation bases.

17. The obstruction detection system according to claim 9, wherein the monitoring means monitors the at least one catheter and the at least one sheath manipulation bases by means of a CANOpen protocol standard.

18. An obstruction detection system for a robotic catheter system including a robotic catheter manipulator assembly including a catheter manipulation base and a sheath manipulation base, the obstruction detection system comprising: an electronic control system configured to control movement of the catheter manipulation base and the sheath manipulation base and to receive a signal indicating information relating to the catheter manipulation base and the sheath manipulation base; wherein the electronic control system is configured to determine a relative distance between the catheter manipulation base and the sheath manipulation base, and wherein the electronic control system configured to determine if the relative distance between the catheter and sheath manipulation bases is less than a predetermined distance, wherein if the relative distance is less than the predetermined distance, then indicating an obstruction status of the catheter and sheath manipulation bases as obstructed, and stopping motion of the catheter and sheath manipulation bases, wherein if the relative distance is greater than or equal to the predetermined distance, then indicating the obstruction status of the catheter and sheath manipulation bases as unobstructed, and allowing motion of the catheter and sheath manipulation bases.

* * * * *